(12) United States Patent
De Soto

(10) Patent No.: US 10,532,184 B2
(45) Date of Patent: Jan. 14, 2020

(54) MODULAR CATHETER PACKAGING

(71) Applicant: BIOSENSE WEBSTER (ISRAEL) LTD., Yokneam (IL)

(72) Inventor: John Aldo De Soto, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/393,126

(22) Filed: Dec. 28, 2016

(65) Prior Publication Data
US 2018/0177977 A1     Jun. 28, 2018

(51) Int. Cl.
| | |
|---|---|
| A61B 50/33 | (2016.01) |
| A61M 25/00 | (2006.01) |
| A61B 50/20 | (2016.01) |
| B65B 5/02 | (2006.01) |
| B65B 5/04 | (2006.01) |
| B65C 1/02 | (2006.01) |
| B65D 25/10 | (2006.01) |
| B65D 43/02 | (2006.01) |

(Continued)

(52) U.S. Cl.
CPC .......... *A61M 25/002* (2013.01); *A61B 17/865* (2013.01); *A61B 50/20* (2016.02); *A61B 50/33* (2016.02); *B65B 5/02* (2013.01); *B65B 5/04* (2013.01); *B65C 1/02* (2013.01); *B65D 25/102* (2013.01); *B65D 43/02* (2013.01); *B65D 81/107* (2013.01); *A61B 90/90* (2016.02); *A61B 2050/0065* (2016.02)

(58) Field of Classification Search
CPC .... A61M 25/002; A61B 50/33; B65D 25/102; B65D 25/106; B65D 73/0014; B65D 73/005

USPC .... 206/438, 364, 303, 304.2, 388, 49, 459.5
See application file for complete search history.

(56) References Cited

U.S. PATENT DOCUMENTS

| | | | |
|---|---|---|---|
| 3,052,812 A * | 9/1962 | Dow | H05B 33/26 313/511 |
| 4,068,757 A | 1/1978 | Casey | |

(Continued)

FOREIGN PATENT DOCUMENTS

| | | | |
|---|---|---|---|
| CN | 201559433 U | * | 8/2010 |
| WO | WO 2010/068587 A2 | | 6/2010 |

OTHER PUBLICATIONS

European Search Report dated May 22, 2018, Application No. EP 17 21 0723.

*Primary Examiner* — Allan D Stevens

(57) ABSTRACT

A catheter packaging includes a catheter tray, having a bottom, a raised edge connected to and surrounding the bottom, a first matrix of holes perforated through the bottom, and a protuberance protruding above a portion of the bottom, the protuberance being dimensioned to raise a distal end of a catheter attached to the protuberance by a predetermined height above the bottom. The protuberance includes a second matrix of holes perforated through the protuberance. The catheter packaging further includes first ties, configured to secure the catheter to the bottom of the catheter tray by threading the first ties through selected holes of the first matrix and tying the first ties around the catheter, and second ties, configured to secure the distal end of the catheter to the protuberance by threading the second ties through selected holes of the second matrix and tying the second ties around the distal end.

10 Claims, 6 Drawing Sheets

(51) Int. Cl.
  *B65D 81/107* (2006.01)
  *A61B 17/86* (2006.01)
  *A61B 50/00* (2016.01)
  *A61B 90/90* (2016.01)

(56) References Cited

U.S. PATENT DOCUMENTS

| | | | |
|---|---|---|---|
| 4,523,679 A | 6/1985 | Paikoff et al. | |
| 4,779,727 A | 10/1988 | Taterka et al. | |
| 4,925,448 A | 5/1990 | Bazaral | |
| 4,976,351 A * | 12/1990 | Mangini | G09F 3/0288 |
| | | | 206/232 |
| 5,238,631 A * | 8/1993 | Stolk | B65D 63/12 |
| | | | 264/147 |
| 5,792,422 A * | 8/1998 | Lin | A61L 2/14 |
| | | | 134/186 |
| 5,848,691 A * | 12/1998 | Morris | A61M 25/002 |
| | | | 206/364 |
| 6,053,313 A | 4/2000 | Farrell et al. | |
| 6,068,121 A | 5/2000 | McGlinch | |
| 6,892,881 B2 | 5/2005 | Leitch | |
| 7,410,053 B2 * | 8/2008 | Bowen | B25H 3/06 |
| | | | 206/370 |
| 7,491,176 B2 | 2/2009 | Mann | |
| 7,743,918 B2 | 6/2010 | Itou et al. | |
| 8,631,935 B2 | 1/2014 | Tomes et al. | |
| 8,662,306 B2 | 3/2014 | Agrawal | |
| D720,471 S | 12/2014 | Angel et al. | |
| 9,283,352 B2 | 3/2016 | Tomes et al. | |
| 2006/0109118 A1 * | 5/2006 | Pelo | G06K 19/077 |
| | | | 340/572.1 |
| 2010/0293892 A1 * | 11/2010 | Curry | A61B 5/14532 |
| | | | 53/403 |
| 2011/0290260 A1 | 12/2011 | Tomes et al. | |
| 2012/0103840 A1 | 5/2012 | McCaffrey | |
| 2014/0110296 A1 | 4/2014 | Terzibashian | |
| 2016/0038713 A1 | 2/2016 | Kearns et al. | |
| 2016/0228676 A1 * | 8/2016 | Glithero | A61M 25/002 |

* cited by examiner

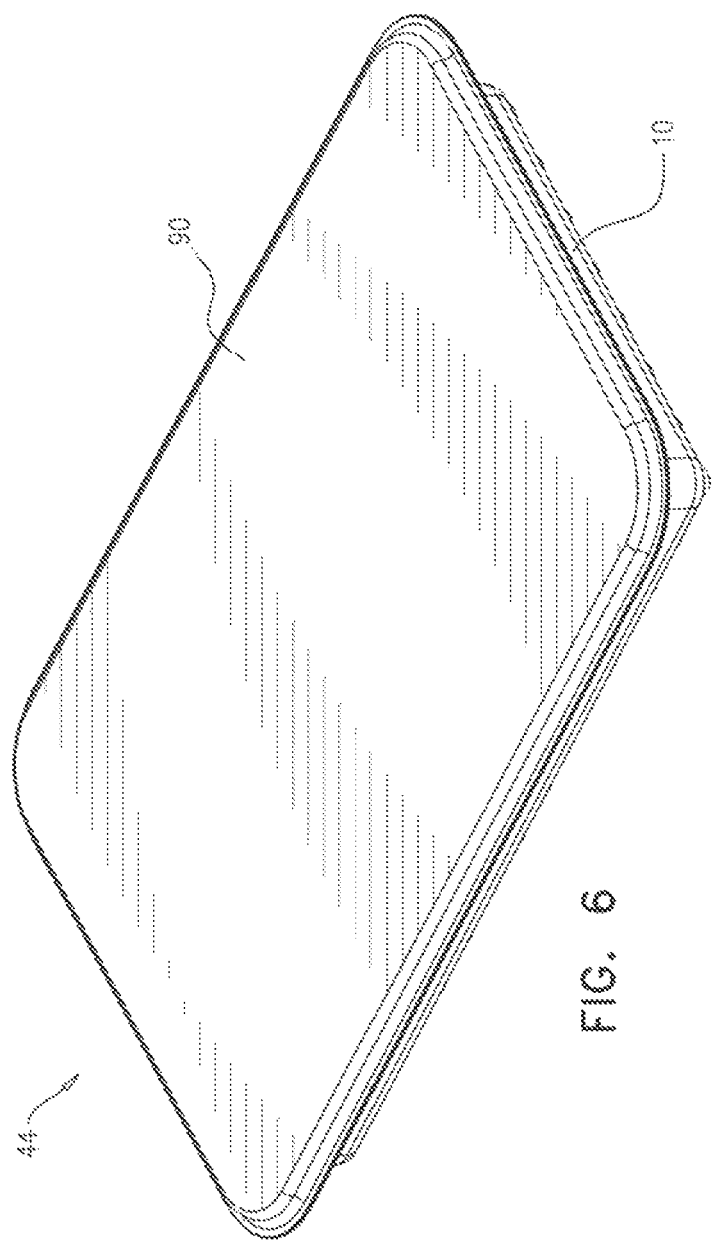

MODULAR CATHETER PACKAGING

FIELD OF THE INVENTION

The present invention relates generally to medical devices, and particularly to medical catheters.

BACKGROUND

Catheters are used in many medical applications and procedures, such as catheter ablation, urinary catheterization, angioplasty, and internal pressure measurements. The packaging of the catheters typically has to comply with multiple requirements.

U.S. Pat. No. 4,779,727, which is incorporated herein by reference, describes a catheter packaging system that includes a catheter tray having a main tray body with a hub-retaining portion and an interchangeable catheter tip-retaining insert. The insert is selectively receivable within a corresponding recess in the main tray body. The main tray body and the interchangeable insert each include a plurality of catheter tracks for holding different catheters with at least one catheter tip track of the interchangeable insert being in line with a main body track for holding a catheter therein. Each main body track is provided with a hub-retaining slot for engaging and holding a catheter hub.

U.S. Pat. No. 6,068,121, which is incorporated herein by reference, describes a generally flat packaging tray for containing an elongated catheter device in an ordered coiled arrangement. The tray includes a recessed channel system formed within and including a plurality of spaced generally parallel, level, generally linear channel sections of two different depths joined by a plurality of arcuate channel sections some of which are inclined between the two depths and are configured to contain catheter devices of a variety of lengths and French sizes nested therein in a coiled arrangement.

U.S. Pat. No. 6,892,881, which is incorporated herein by reference, describes a packaging system for an elongate medical device that includes a sheet of material which defines a generally planar surface for receiving the elongated medical device thereon. A plurality of butterfly tabs are adhesively attached to the planar surface at selected locations to retain the medical device in position. The butterfly tabs are stated to eliminate weaving of catheters onto mounting cards having tabs punched therethrough.

U.S. Pat. No. 8,631,935, which is incorporated herein by reference, describes a tray for accommodating a coiled medical device, such as a catheter assembly, which includes a first compartment, a second compartment, and a third compartment. The catheter assembly and devices associated with a catheterization procedure, such as syringes containing sterile water and lubricating jelly and a specimen container can be disposed within the tray. A first barrier and second barrier separate the compartments. The barriers can have openings therein to accommodate large syringes or to enable the first compartment to be used as a lubricant applicator for the catheter. The first compartment can include a stair-stepped contour such that the syringes are held at different depths to facilitate ease of use. The various devices can be disposed within the tray in accordance with their order of use in the catheterization procedure.

U.S. Pat. No. 8,662,306, which is incorporated herein by reference, describes how different length and diameter size catheters may be packaged in a universal catheter tray assembly that utilizes identical base trays. Catheter size selectors, which include a size indicium formed therein, are snap connected to the base tray and define at least a portion of a catheter capture channel with an opening width corresponding to the size indicium. The universal catheter tray assembly is configured for packaging a catheter with a size corresponding to the size indicium and with any one of a plurality of tip shapes such that first and second segments of the catheter are confined in first and second catheter capture channels, respectively.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY

Embodiments of the present invention that are described hereinbelow provide catheter packaging that accepts catheters of different shapes and sizes.

There is therefore provided, in accordance with an embodiment of the present invention, an apparatus for catheter packaging, including a catheter tray having a bottom, a raised edge connected to and surrounding the bottom, a first matrix of holes perforated through the bottom of the catheter tray, and a protuberance protruding above a portion of the bottom, the protuberance being dimensioned to raise a distal end of a catheter attached to the protuberance by a predetermined height above the bottom, and the protuberance including a second matrix of holes perforated through the protuberance. The apparatus further includes first ties, configured to secure the catheter to the bottom of the catheter tray by threading the first ties through selected holes of the first matrix and tying the first ties around the catheter, and second ties, configured to secure the distal end of the catheter to the protuberance by threading the second ties through selected holes of the second matrix and tying the second ties around the distal end.

In another embodiment the catheter tray and one or more of the first and second ties are manufactured of a sterilizable and biocompatible material.

In yet another embodiment the catheter tray is configured to provide mechanical protection to a catheter secured inside the tray.

In a disclosed embodiment material for one or more of the first and second ties is provided as a spool, and one or more of the first and second ties are cut to predetermined lengths from the spool.

In another embodiment the holes in the first and second matrices are labeled by unique identifiers. Typically, the catheter packaging includes packaging instructions for a given catheter, the packaging instructions identifying the selected holes of the first and second matrices by the unique identifiers and indicating predetermined lengths of the first and second ties for tying the catheter to the holes.

In another embodiment the first and second ties include stainless steel wire coated with polytetrafluoroethylene (PTFE).

In yet another embodiment the bottom of the catheter tray includes a matrix of indentations interspersed between the first matrix of holes.

In still another embodiment the protuberance includes a ramp.

In a disclosed embodiment the protuberance includes one or more foam blocks.

In another embodiment the catheter packaging includes cutout tabs co-planar with the bottom, wherein the cutout tabs bend up from the bottom so as to secure the catheter to the bottom.

There is also provided, in accordance with an embodiment of the present invention, a method for catheter packaging, including providing a catheter tray including a bottom, a raised edge connected to and surrounding the bottom, a first matrix of holes perforated through the bottom of the catheter tray, a protuberance protruding above a portion of the bottom, the protuberance being dimensioned to raise a distal end of a catheter attached to the protuberance by a predetermined height above the bottom, the protuberance including a second matrix of holes perforated through the protuberance. The method further includes providing first ties and second ties. The method further includes securing the catheter to the bottom of the catheter tray by threading the first ties through selected holes of the first matrix and tying the first ties around the catheter, and securing the distal end to the protuberance by threading the second ties through selected holes of the second matrix and tying the second ties around the distal end.

The method may include manufacturing the catheter tray and one or more of the first and second ties of a sterilizable and biocompatible material.

In another embodiment the method includes configuring the catheter tray to provide mechanical protection to a catheter secured inside the tray.

In yet another embodiment the method includes providing material for one or more of the first and second ties as a spool, and cutting the one or more of the first and second ties to predetermined lengths from the spool.

In some embodiments the catheter packaging includes labeling the holes of the first and the second matrices with unique identifiers. Typically, the method includes providing packaging instructions for a given catheter, the packaging instructions identifying the selected holes of the first and second matrices by the unique identifiers and indicating predetermined lengths of the one or more first and second ties for tying the catheter to the holes.

In a disclosed embodiment the first and second ties comprise stainless steel wire coated with polytetrafluoroethylene (PTFE).

In a further embodiment the method includes configuring the bottom of the catheter tray to have a matrix of indentations interspersed between the first matrix of holes.

In a disclosed embodiment the protuberance includes a ramp.

In a further embodiment the protuberance includes one or more foam blocks.

In yet another embodiment the method includes providing cutout tabs co-planar with the bottom, wherein the cutout tabs bend up from the bottom so as to secure the catheter to the bottom.

The present invention will be more fully understood from the following detailed description of the embodiments thereof, taken together with the drawings in which:

BRIEF DESCRIPTION OF THE DRAWINGS

FIG. 6 is a schematic illustration of a portion of the catheter packaging assembly, comprising a lid covering the catheter tray and attached to it, in accordance with an embodiment of the invention.

DETAILED DESCRIPTION OF EMBODIMENTS

Overview

The packaging of medical catheters is required to be sterile and fully biocompatible. In addition, the packaging has to protect the catheter from any undue bending or twisting, as these could damage the physical integrity of the catheter, and consequently prevent a successful insertion of the catheter into a lumen in a patient's body.

In developing new catheters, a so-called first-in-man study, for example, requires that the prototype catheter be packaged in fully biocompatible and sterile packaging, which will also afford the catheter mechanical protection. If the prototype does not fit in existing catheter packaging, new packaging has to be developed for the prototype. This kind of customization, however, is both expensive and time consuming, and will not in general comply with the budgetary constraints or timeline of a catheter development project. Consequently, using only existing packaging designs limits the innovation and development of novel catheters to prototypes that fit in the existing packaging.

Embodiments of the present invention that are described herein provide catheter packaging. This packaging accepts a wide variety of shapes and sizes of catheters, and thus relieves a project that develops novel and new catheters from the requirement of complying with the tight packaging constraints imposed by catheter-specific packaging designs.

In one embodiment a catheter packaging comprises a catheter tray having a bottom and a raised edge connected to and surrounding the bottom. A first matrix of holes perforate the bottom, and there is a protuberance that protrudes from a portion of the bottom. The protuberance is dimensioned to raise the distal end of a catheter attached to the protuberance by a predetermined height above the bottom, and the protuberance has a second matrix of holes perforating the protuberance.

The catheter packaging further comprises first ties that secure the catheter to the bottom of the catheter tray by threading the first ties through selected holes of the first matrix and by tying the first ties around the catheter. The packaging also comprises second ties that secure the distal end of the catheter to the protuberance by threading the second ties through selected holes of the second matrix and by tying the second ties around the distal end.

The design of the catheter packaging enables securing different shapes of catheter handles or devices, including ones that have complicated and difficult-to-secure features, such as those with multiple pigtail attachments.

System Description

Figure 1:
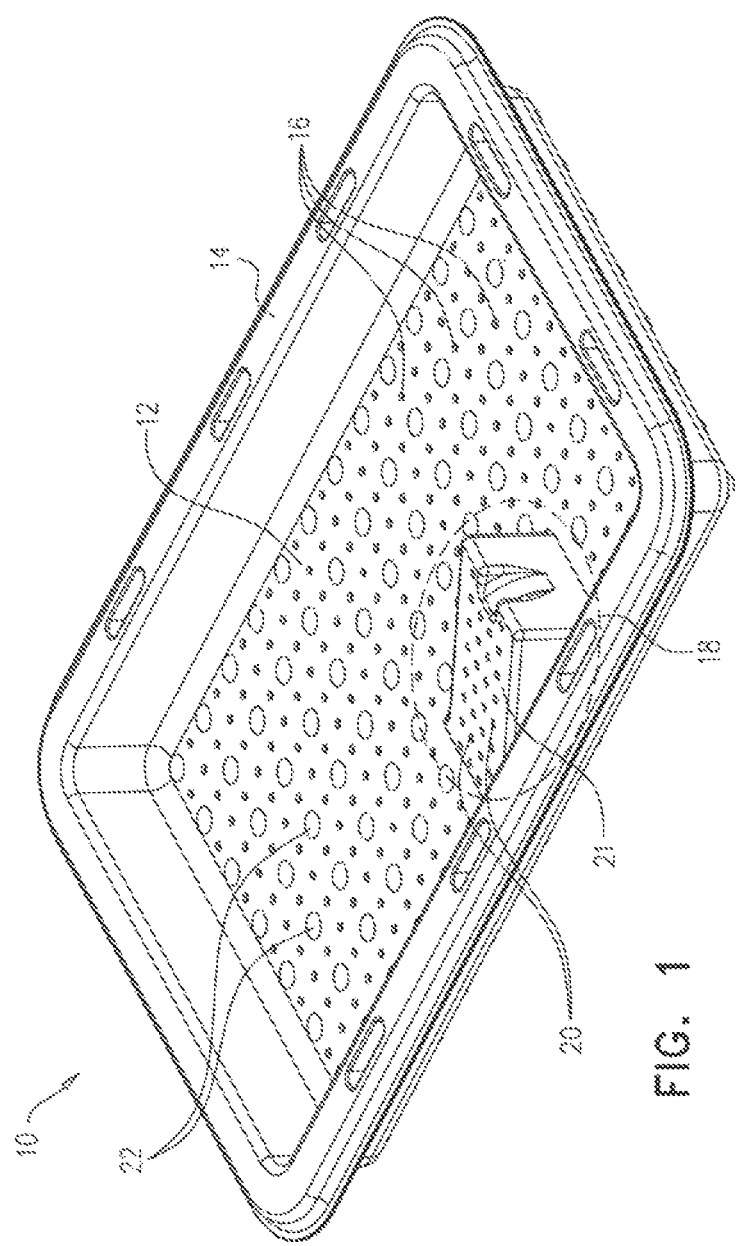
FIG. 1 is a schematic illustration of a catheter tray, in accordance with an embodiment of the invention.
Figure 2:
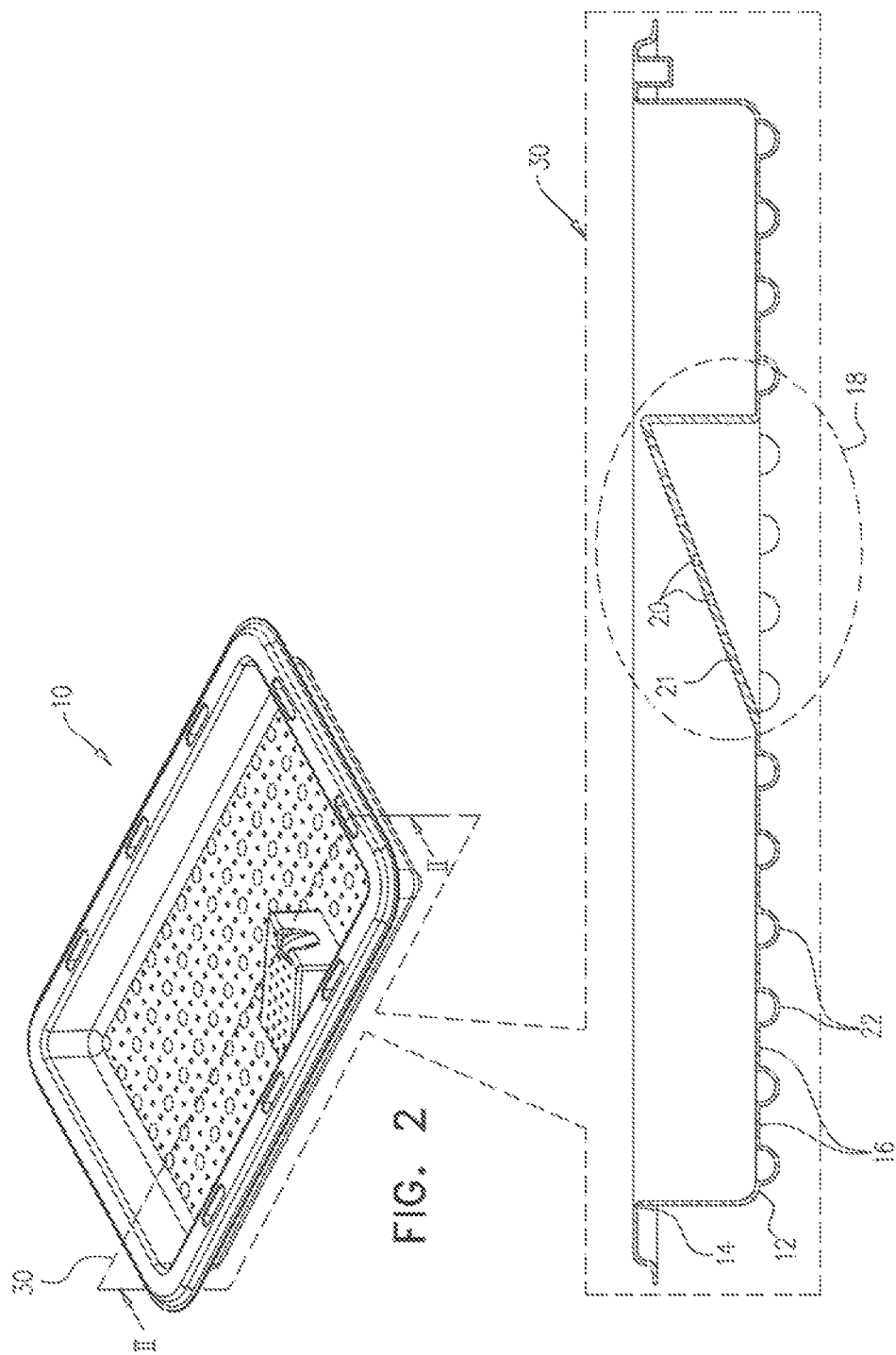
FIG. 2 is a schematic cross-section of a catheter tray, in accordance with an embodiment of the invention.

FIG. 1 is a schematic illustration of a catheter tray 10, and FIG. 2 is a schematic cross-section of the tray, in accordance with an embodiment of the invention. Catheter tray 10 is manufactured of a biocompatible, sterilizable and stiff material, such as polystyrene, polyethylene terephthalate (PET) or polyethylene terephthalate glycol-modified (PETG), providing mechanical support and protection to a catheter to be secured in the tray (the positioning of the catheter is described in FIG. 4). Catheter tray 10 comprises a bottom 12 and a raised edge 14. Holes 16 are perforated in a matrix through bottom 12 to provide for securing the catheter. On a part of bottom 12 is located a ramp 18, which protrudes above bottom 12. Ramp 18 may be utilized to raise the distal end of the catheter above bottom 12 to a predetermined height. Holes 20 are perforated in a matrix through an inclined surface 21 of ramp 18 to provide for securing the catheter. A matrix of indentations 22, for instance of hemispherical shape, are provided in bottom 12, interspersed between holes 16. Indentations 22 reduce the contact area between the catheter and bottom 12 and reduce the contact area between the underside of catheter tray 10 and that upon which it lies (such as the sterile pouch). The interspersed hemispheres also offset the pouch so that it does not make contact with or become entangled in the twisted ties that loop through the backside. FIG. 2 is a schematic cross-section 30 of catheter tray 10, taken along a plane II-II of the tray.

Figure 3:
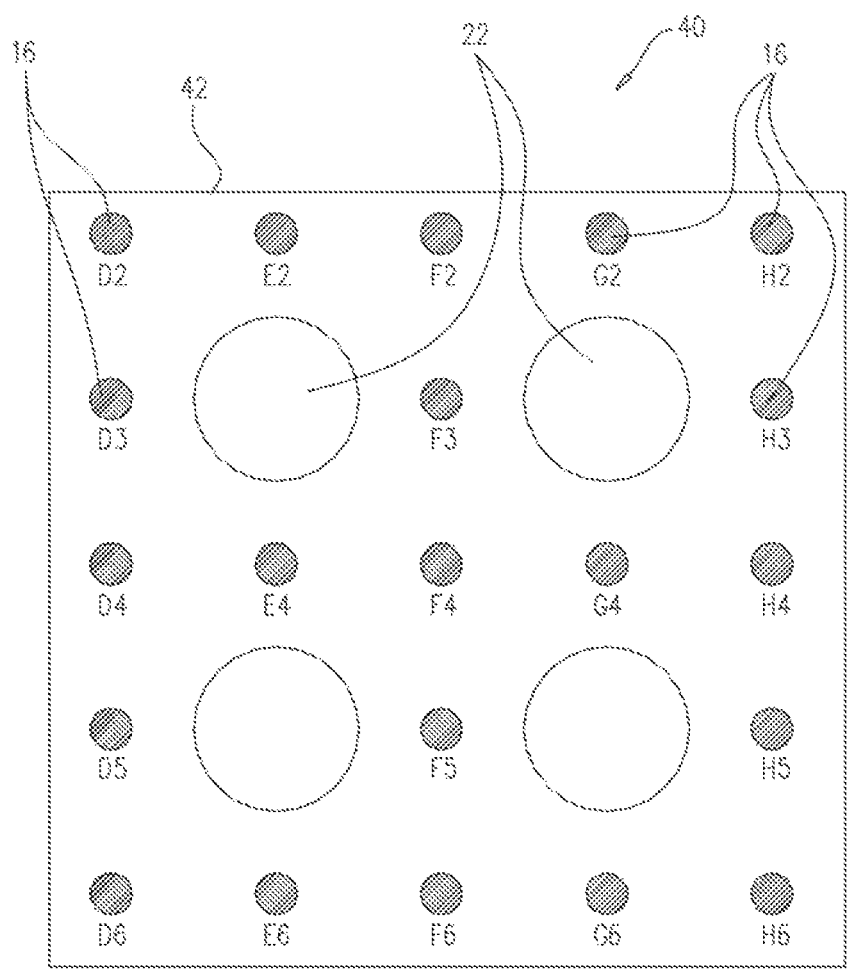
FIG. 3 is a schematic illustration of an identification scheme of holes, in accordance with an embodiment of the invention.

FIG. 3 is a schematic illustration of an identification scheme 40 of holes 16, in accordance with an embodiment of the invention. Identification scheme 40 shows a section 42 of bottom 12, with the section comprising holes 16 and indentations 22. Identification scheme 40 comprises labeling the columns of holes 16 by consecutive letters of the alphabet, and the rows of holes 16 by consecutive integers. The resulting labels are unique identifiers of the holes and are typically printed adjacent to their respective holes on bottom 12. Thus the address of a selected hole 16 is given, for example, as D4, indicating that the hole can be found in column D and row 4. Alternatively, other schemes for addressing or identifying the holes may be used.

A set of packaging instructions is typically provided for packaging a specific catheter in a catheter tray 10. These packaging instructions would use identification scheme 40 for tying down a specific catheter to a specific hole. The packaging instructions would read, for instance, "Use a length of 2" of the tie material between holes D3 and F3."

The tie material typically comprises stainless steel wire coated with polytetrafluoroethylene (PTFE) or other polymer. The metal core material is typically at an annealed temper to ensure that a twisted tie does not unwrap. The tie material may be provided in a spool, from which the required lengths of ties are cut according to the packaging instructions. Alternatively, the tie material is provided in pre-cut lengths, from which the required lengths are selected according to the packaging instructions.

An alternative embodiment comprises elastic bands instead of, or in addition to, the coated stainless steel wire ties. The elastic bands are typically made of latex or rubber.

Figure 4:
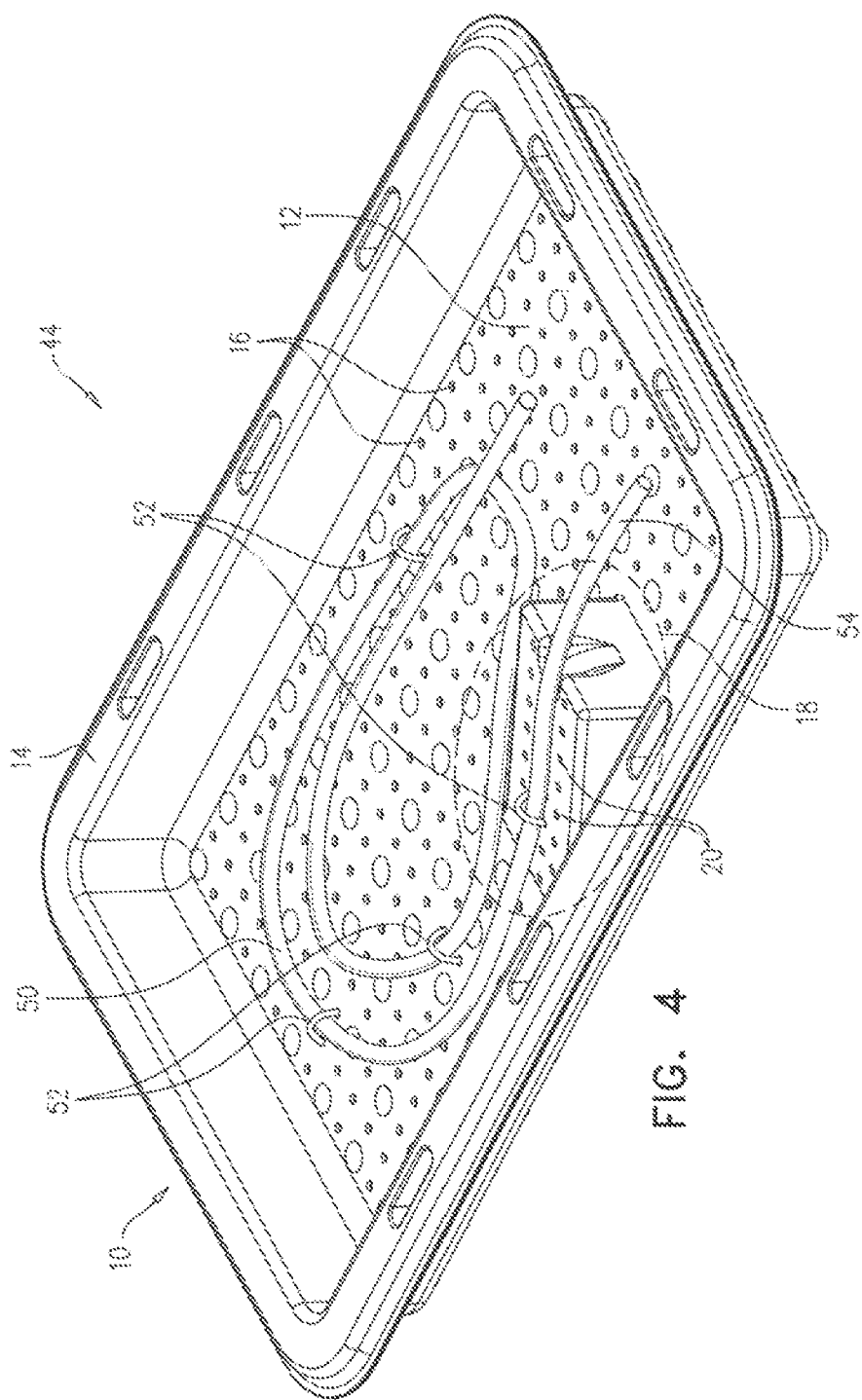
FIG. 4 is a schematic illustration of a catheter packaging assembly, comprising a catheter secured to the bottom of the catheter tray, in accordance with an embodiment of the invention.

FIG. 4 is a schematic illustration of a catheter packaging assembly 44, comprising a catheter 50 secured to bottom 12 of catheter tray 10, in accordance with an embodiment of the invention. Catheter 50 is looped to fit into catheter tray 10 and is secured in place by ties 52. Ties 52 are threaded through selected holes 16 and/or 20 which are located near the catheter. As described in the context of FIG. 3, the addresses of selected holes 16 and 20, as well as the length of ties 52, are typically given in the packaging instructions specific to catheter 50. A distal end 54 of catheter 50 is raised by ramp 18 to a pre-determined height and is typically suspended above bottom 12 to prevent damage to the delicate structure of distal end 54. Alternatively, distal end 54 may be enclosed in protective material (not shown) utilizing the free space around distal end 54.

Figure 5:
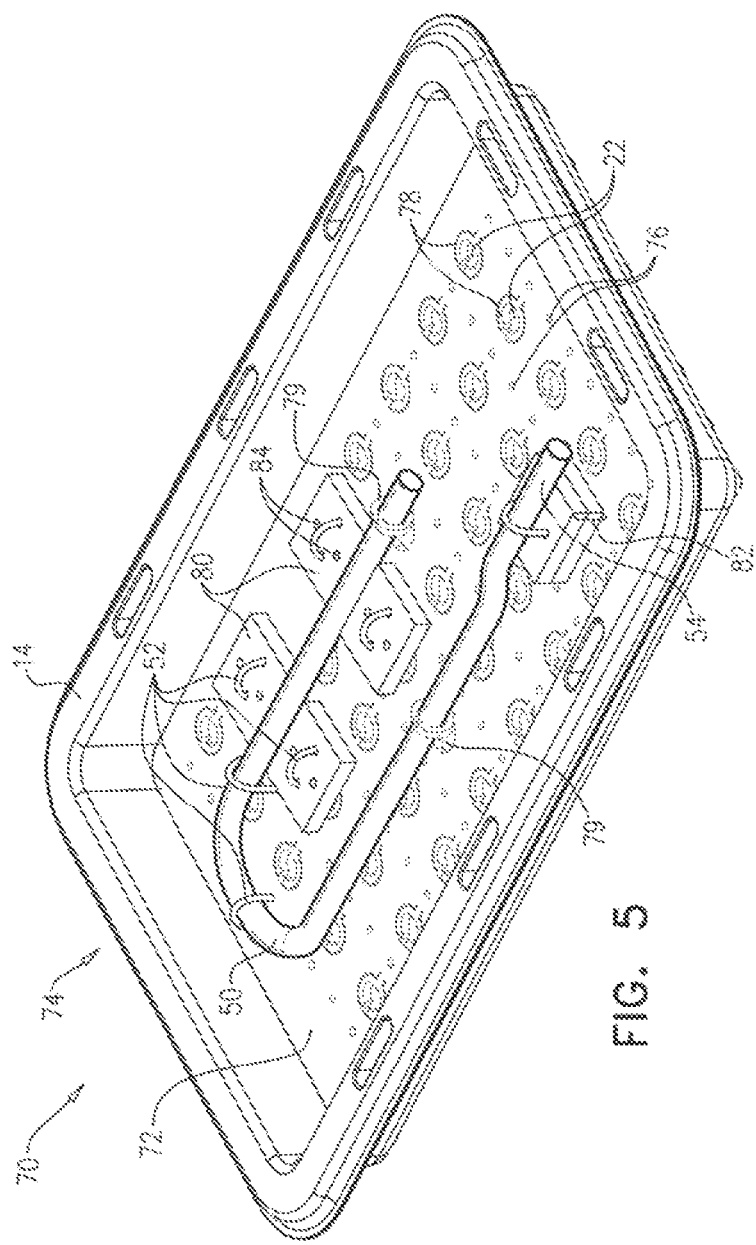
FIG. 5 is a schematic illustration of a catheter packaging assembly, comprising a catheter secured to the bottom of the catheter tray, in accordance with an alternative embodiment of the invention.

FIG. 5 is a schematic illustration of a catheter packaging assembly 70, comprising catheter 50 secured to a catheter tray 74, in accordance with an alternative embodiment of the invention. Apart from the differences described below, the operation of assembly 70 is generally similar to that of assembly 44 (FIGS. 1-4), and elements indicated by the same reference numerals in both assemblies 44 and 70 are generally similar in construction and in operation.

Catheter tray 74 comprises a bottom 72 and raised edge 14. A matrix of holes 76 and cutout tabs 78 are perforated through bottom 72. Holes 76 are generally similar to holes 16 of assembly 44. As manufactured, cutout tabs 78 lie flat on bottom 72, but they are bent up for securing catheter 50 where required, as illustrated by bent-up cutout tabs 79. Cutout tabs 78 are concentric with indentations 22. Cutout tabs 78 are identified using a scheme (not shown) similar to scheme 40 illustrated in FIG. 3.

Holes 76 are provided for securing catheter 50 with ties 52, as well as securing foam blocks 80. Foam blocks 80 are provided for securing catheter 50 in directions parallel to bottom 72. An assembly 82 of one or more foam blocks 80, for example two foam blocks 80 on top of each other, is provided for raising distal end 54 of catheter 50 above bottom 72, so that assembly 82 acts as a protuberance above the bottom. Foam blocks 80 are perforated with holes 84, generally similar to holes 20 of assembly 44, for securing the foam blocks to bottom 72 with ties 52 as well as for securing catheter 50 onto the foam blocks with ties 52.

FIG. 6 is a schematic illustration of a portion of catheter packaging assembly 44, comprising a lid 90 covering a catheter tray, for example catheter tray 10, and attached to it, in accordance with an embodiment of the invention. Lid 90 is manufactured of a biocompatible, sterilizable and stiff material, such as polystyrene, PET, or PETG, providing protection to a catheter secured in the tray. Catheter tray 10 and lid are further enclosed in a packaging sleeve (not shown). The packaging sleeve is closed against outside contamination, but is gas permeable to permit sterilization. A typical material for the packaging sleeve is TYVEK, flashspun high-density polyethylene fibers, from DuPont Corporation.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A catheter packaging comprising:
   a catheter tray comprising:
      a bottom;
      a raised edge connected to and surrounding the bottom;
      a first matrix of holes perforated through the bottom of the catheter tray; and
      a protuberance protruding above a portion of the bottom, the protuberance being dimensioned to raise a distal end of a catheter attached to the protuberance by a predetermined height above the bottom, the protuberance comprising a second matrix of holes perforated through the protuberance;

first ties, configured to secure the catheter to the bottom of the catheter tray by threading the first ties through selected holes of the first matrix and tying the first ties around the catheter;

second ties, configured to secure the distal end of the catheter to the protuberance by threading the second ties through selected holes of the second matrix and tying the second ties around the distal end; and wherein the holes in the first and second matrices are labeled by unique identifiers.

2. The catheter packaging according to claim 1, wherein the catheter tray and one or more of the first and second ties are manufactured of a sterilizable and biocompatible material.

3. The catheter packaging according to claim 1, wherein the catheter tray is configured to provide mechanical protection to the catheter secured inside the tray.

4. The catheter packaging according to claim 1, wherein material for one or more of the first and second ties is provided as a spool, and wherein one or more of the first and second ties are cut to predetermined lengths from the spool.

5. The catheter packaging according to claim 1, and comprising packaging instructions, the packaging instructions identifying the selected holes of the first and second matrices by the unique identifiers and indicating predetermined lengths of the first and second ties for tying the catheter to the holes.

6. The catheter packaging according to claim 1, wherein the first and second ties comprise stainless steel wire coated with polytetrafluoroethylene (PTFE).

7. The catheter packaging according to claim 1, wherein the bottom of the catheter tray comprises a matrix of indentations interspersed between the first matrix of holes.

8. The catheter packaging according to claim 1, wherein the protuberance comprises a ramp.

9. The catheter packaging according to claim 1, wherein the protuberance comprises one or more foam blocks.

10. The catheter packaging according to claim 1, and comprising cutout tabs co-planar with the bottom, wherein the cutout tabs are configured to bend up from the bottom to secure the catheter to the bottom.

* * * * *